United States Patent [19]
Alchas et al.

[11] Patent Number: 5,334,144
[45] Date of Patent: Aug. 2, 1994

[54] SINGLE USE DISPOSABLE NEEDLELESS INJECTOR

[75] Inventors: Paul G. Alchas, Wayne; A. Wes Prais, Hewitt, both of N.J.

[73] Assignee: Becton, Dickinson and Company, Franklin Lakes, N.J.

[21] Appl. No.: 969,624

[22] Filed: Oct. 30, 1992

[51] Int. Cl.$^5$ .............................................. A61M 5/30
[52] U.S. Cl. ..................... 604/68; 604/110; 604/111; 604/135
[58] Field of Search ................. 604/68, 70, 110, 111, 604/131, 134, 135; 606/182

[56] References Cited

U.S. PATENT DOCUMENTS

| | | | |
|---|---|---|---|
| 1,835,122 | 12/1931 | Thevenot | 604/135 |
| 2,704,543 | 3/1955 | Scherer | 604/68 |
| 3,789,844 | 2/1974 | Burges | 604/135 |
| 4,722,728 | 2/1988 | Dixon | 604/68 |
| 4,752,288 | 6/1988 | Hussey | 604/111 |
| 4,874,367 | 10/1989 | Edwards | 604/72 |
| 4,886,497 | 12/1989 | Scholl, Jr. | 604/111 |
| 4,913,699 | 4/1990 | Parsons | 604/70 |
| 4,941,880 | 7/1990 | Burns | 604/143 |
| 5,009,637 | 4/1991 | Newman et al. | 604/68 |
| 5,026,388 | 6/1991 | Ingalz | 606/182 |
| 5,062,830 | 11/1991 | Dunlap | 604/68 |
| 5,071,353 | 12/1991 | van der Wal | 604/135 |
| 5,135,496 | 8/1992 | Vetter et al. | 604/111 |

*Primary Examiner*—C. Fred Rosenbaum
*Assistant Examiner*—Michael Rafa
*Attorney, Agent, or Firm*—Arthur D. Dawson

[57] ABSTRACT

A single use needleless hypodermic injector includes an elongate housing with a proximal end, a distal end, an axis and a hollow bore therethrough. The housing has a reservoir at the distal end with a generally cylindrical chamber for containing an injectable liquid. The chamber has a axis aligned with the housing longitudinal axis. The chamber has a first open end adjacent the housing with a resilient stopper mounted therein. The reservoir has a distal second end with an orifice in fluid communication with the chamber. The resilient stopper seals the chamber and ejects the liquid from the chamber, forming a stream at the orifice when the stopper is moved distally in the chamber. The injector has an piston mounted for axial movement within the housing bore and elements to axially bias the piston distally within the bore. The piston has an armed position wherein it is positioned proximally within the bore. The injector has elements to retain the piston in the armed position and to release the piston from the armed position. When the injector release elements are released, the piston moves distally to engage and move the resilient stopper distally, ejecting the liquid in the chamber through the orifice in a stream which will make a hypodermic penetration when the orifice is placed adjacent dermal tissue. The injector further has elements which prevent the piston from being retained in the armed position once the release elements are released, thereby rendering the injector non-resuable.

27 Claims, 5 Drawing Sheets

FIG-4

FIG-8

SINGLE USE DISPOSABLE NEEDLELESS INJECTOR

BACKGROUND OF THE INVENTION

1. Field of the Invention

This invention relates generally to hypodermic injection devices, and more particularly to a single use needleless injection device that utilizes a fine high pressure stream of the liquid medicament to penetrate the skin and deliver the desired dosage into a patient's body.

2. Description of Related Information

The needleless jet injection art dates from the 1940's. The ability to perform needleless hypodermic penetrations developed as a result of observations of accidental injection of fluids into workers handling high pressure hydraulic lines having pinhole leaks.

The resultant early jet injector devices actually commercialized tended toward being large, complex units generally adapted to retain sufficient quantities of medicament for repeated injections. Most of these devices were intended for usage in fixed site situations such as army induction centers or mass inoculations at clinics.

Smaller portable devices also have been developed which are powered by compressed gas or springs. For the most part, these devices are complex and multi-component as well as requiring dismantling, reassembly and sterilization between uses.

Attempts have been made to simplify the usage of needleless injectors and make them more practical for individuals required to self-administer medicaments. Several devices have been developed with single use cartridges containing a liquid medicament intended for use with a reusable driver mechanism. Representative of these are U.S. Pat. No. 4,874,367 which teaches a single use cartridge and a reusable spring powered driver mechanism and U.S. Pat. No. 4,941,880 which teaches a prefilled medicament ampule with a reusable compressed gas powered drive mechanism. The devices taught in the '367 and '880 patents are complex and multi-component. They have a mass and size similar to a two cell "C" flashlight.

A single use device employing a gas powered drive mechanism is taught in U.S. Pat. No. 5,009,637. The teachings describe a threaded socket for a filled vial to vary the dose delivered. The '637 device has numerous parts and requires a fracturable high pressure cylinder or ampule to contain the compressed gas.

Size and complexity of the drive mechanism has largely precluded the use of needleless injectors for stand-by self administration of medicaments for acute insect bite allergy reactions, migraine attacks, infertility, impotence and the like. The majority of the devices in the prior art are designed to be reusable, hence they must be reloadable, thereby increasing their physical complexity and mass. As a result, most stand-by self administration kits currently available use either prefilled hypodermic syringes, or sealed ampules and a standard hypodermic syringe. While these kits are satisfactory for their intended use, in many states possession and disposal of syringes is regulated, thereby affecting their availability and use. Further, self administration of an injectable medicament, either with a prefilled syringe or a sealed ampule with a standard syringe, particularly under conditions of a physical stress such as an allergy or migraine attack requires a high level of control and skill on the part of the patient. A single use prefilled needleless hypodermic injection device which was simple to use, not complex to manufacture, hence available at a reasonable cost, designed not to be reuseable, thus likely not subject to the regulatory requirements regarding possession and disposal of hypodermic syringes, would represent an advance to the art. Such a device is described hereinbelow.

SUMMARY OF THE INVENTION

An operable single use needleless hypodermic injector includes an elongate housing with a proximal end, a distal end, a longitudinal axis and a hollow bore therethrough. The housing has a reservoir at the distal end of the housing with a generally cylindrical chamber for containing an injectable liquid. The reservoir has a longitudinal axis axially aligned with the housing longitudinal axis and has a first open end adjacent the housing with a resilient stopper mounted slidably therein. The reservoir has a distal second end with an orifice in fluid communication with the chamber. The resilient stopper serves to seal the chamber and to eject the liquid from the chamber, forming a stream at the orifice when the stopper is moved distally in the chamber. An elongate piston is mounted for axial movement within the housing bore. The injector has elements for axially biasing the piston distally within the bore. The piston has an armed position wherein it is positioned proximally within the bore in opposition to the biasing elements. Further the injector has elements to retain the piston in the armed position causing the biasing elements to have potential energy and elements to release the piston from the armed position thereby allowing the energy of the biasing elements to urge a distal axial movement of the piston. With a distal movement, the piston engages and causes a distal axial movement of the stopper through the chamber which ejects the liquid through the orifice forming a stream of the liquid which will make a hypodermic penetration when the orifice is placed adjacent dermal tissue. The injector further has elements which prevent the piston from being retained in the armed position after the release elements are released.

In one embodiment, the biasing elements for distally axially biasing the piston include a helical compression spring coaxially mounted about the piston. The spring is compressed between the housing and the piston when the piston is in the armed position. The axial force necessary to compress the spring is applied to the housing primarily as a radial force by the retention elements so that the housing central portion is not under any substantial axial load when the piston is retained in the armed position.

The injector housing includes an annular inwardly directed shoulder defining an inner dimension transverse the housing axis. The elongate piston has at least two cantilevers extending proximally therefrom. Each cantilever has a radially outwardly directed projection for engaging the shoulder and a radially inwardly directed protuberance. The cantilevers define a recess in the piston having an inside dimension transverse to the longitudinal axis. The elongate piston has an elongate plunger with a proximal end and a distal end positioned for slidable movement within the recess. The plunger has a large dimension portion transverse the longitudinal axis and a small dimension portion transverse the longitudinal axis located proximally adjacent to the large dimensional portion. When the plunger is positioned so that the large dimension portion contacts the protuberances on the cantilevers and the piston is in the armed position, inward flexion of the cantilever is prevented and the projections on the cantilevers engage the shoulder on the housing retaining the piston in the armed position. The piston is releasable from the armed position by application of a distal axial force which causes axial movement of the plunger relative to the protuberances so that the small dimension portion of the plunger is adjacent to the protuberances on the cantilevers. The positioning of the small dimension portion of the plunger adjacent the cantilever protuberances allows inward flexion of the cantilevers disengaging the projections from the shoulder and releasing the piston. With the protuberances on the cantilevers being adjacent the small dimension portion, the plunger is contained in the recess by the protuberances on the cantilevers and the plunger is withdrawn into the housing with the distal movement of the piston. This withdrawal into the housing will substantially prevent the piston from being retained in the armed position thereby substantially preventing reuse of the injector.

DETAILED DESCRIPTION OF THE INVENTION

While this invention is satisfied by embodiments in many different forms, there is shown in the drawings and will herein be described in detail preferred embodiments of the invention with the understanding that the present disclosure is to be considered exemplary of the principles of the invention and is not intended to limit the invention to the embodiments illustrated. The scope of the invention will be measured by the appended claims and their equivalents.

The single use needleless injector of the present invention is illustrated in FIGS. 1-9 and is generally designated as 20.

For the purposes of the description of the present invention the "distal end" is meant to refer to the end of the device closest to the delivery end of the device, and "proximal end" is meant to refer to the end of the device furthest from the delivery end of the device. Referring to FIGS. 1-4, injector 20 includes an elongate housing 22 having a central portion 23 with a hollow bore 24 and a longitudinal axis A, a proximal end 26 and a distal end 28. Housing 22 has a reservoir 30 mounted at distal end 28. The reservoir has a generally cylindrical chamber 32 defining a longitudinal axis B generally aligned with longitudinal axis A of housing 22 for containing an injectable liquid 33. Chamber 32 of reservoir 30 has a first open end 34 adjacent housing 22 with a resilient stopper 36 mounted therein for slidable movement. Reservoir 30 has a second end 40 having an orifice 42 in fluid communication with chamber 32. Stopper 36 seals chamber 32 and with distal movement ejects injectable liquid 33 through orifice 42. Orifice 42 serves to form a stream S of liquid 33 when stopper 36 is moved distally in chamber 32.

Injector 20 further includes an elongate piston 44 mounted for axial movement within bore 24. Piston 44 has a proximal end 46 and a distal end 48. Injector 20 has a biasing element to axially bias piston 44 to distal end 28 of housing 22. In a preferred embodiment shown in FIGS. 1 and 4-7, the biasing element is a helical spring 50 coaxially mounted around piston 44.

Figure 1:
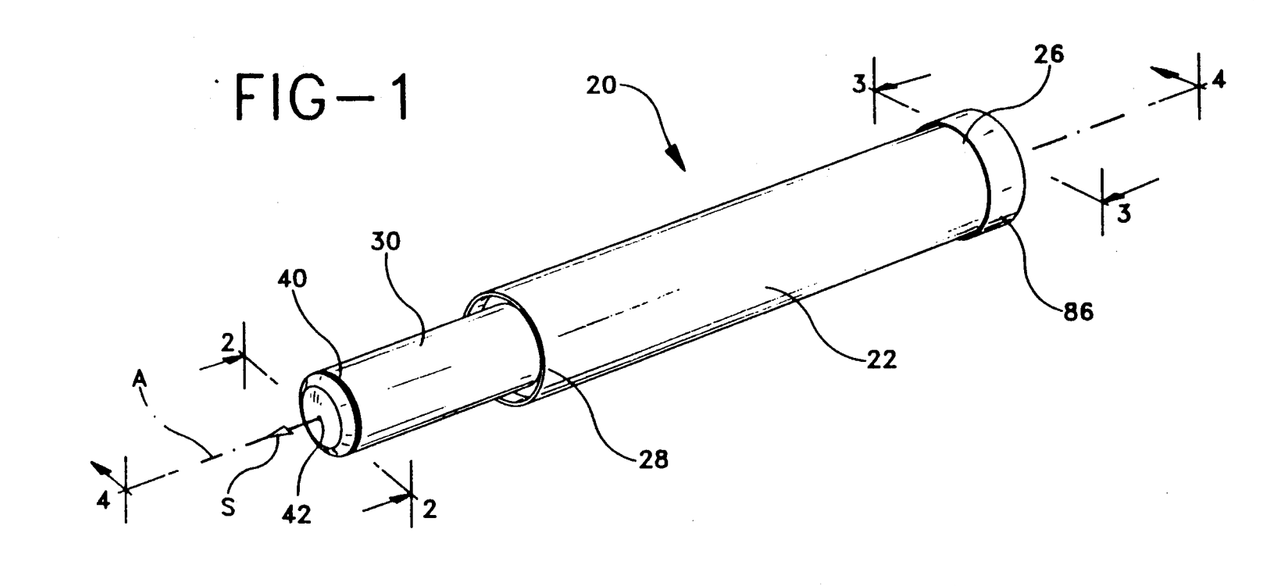
FIG. 1 is a perspective view of the needleless injector of the present invention.
Figure 2:
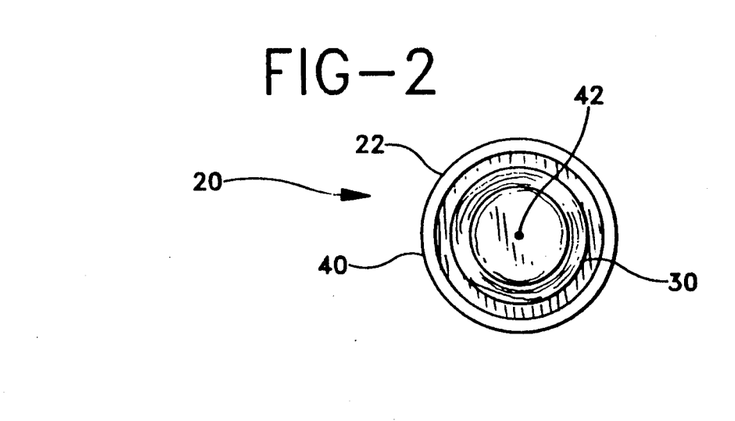
FIG. 2 is a side elevation view of the needleless injector of FIG. 1 viewed from the distal end.
Figure 3:
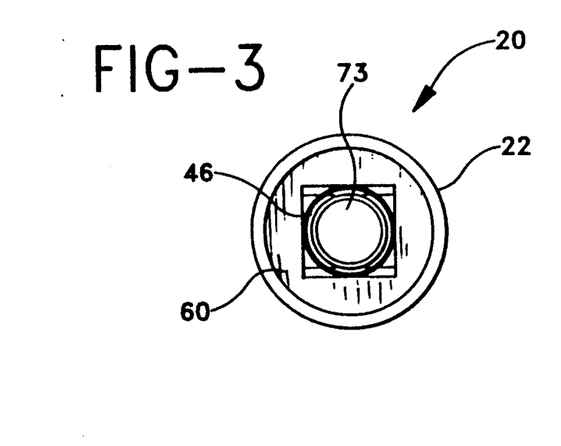
FIG. 3 is a side elevation view of the needleless injection of FIG. 1 viewed from the proximal end.
Figure 4:
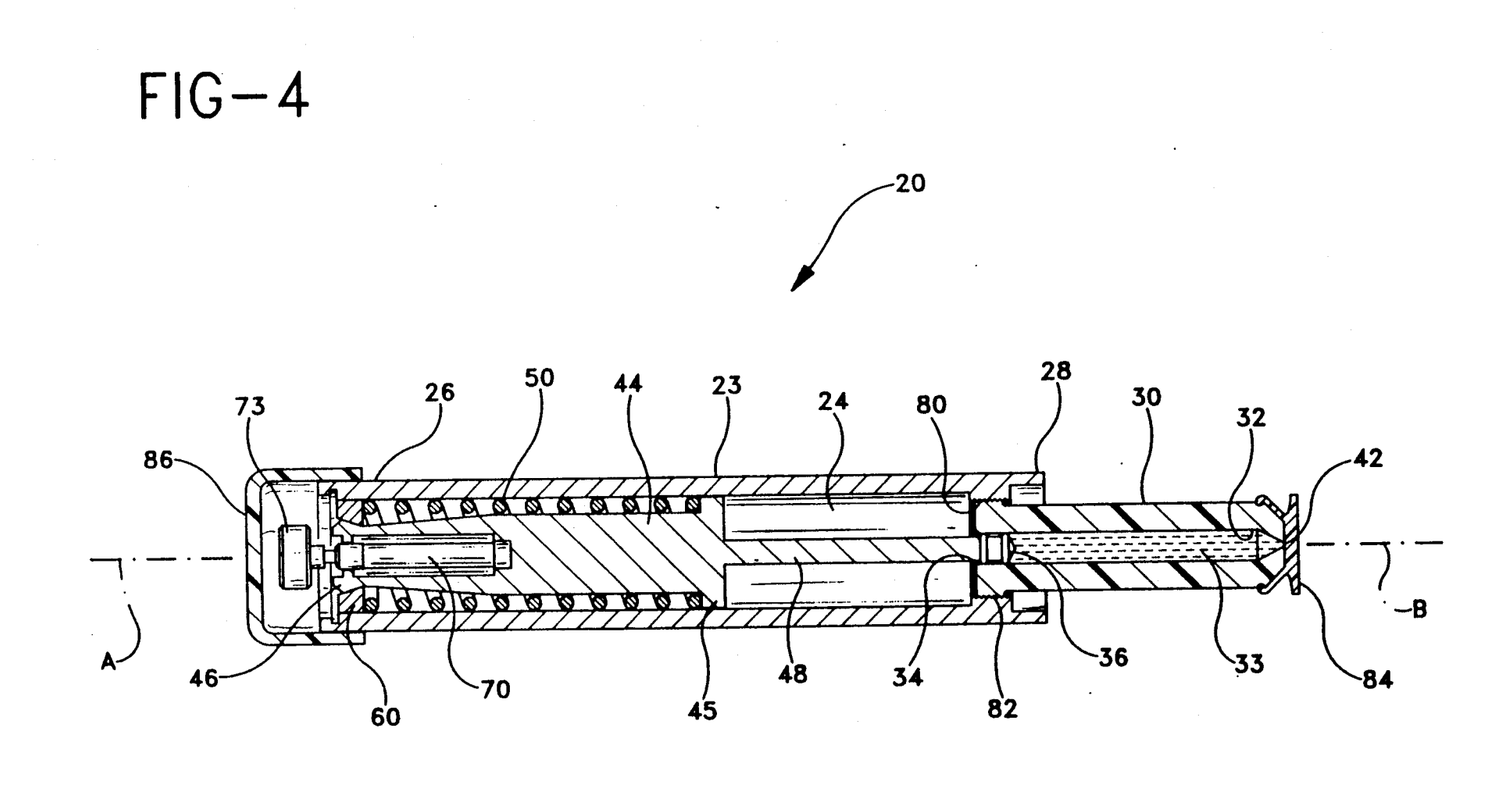
FIG. 4 is a cross-sectional view of the injector of FIG. 1 taken along the line 4, 4.

Piston 44 has an armed position, as shown in FIG. 4, where piston 44 is positioned at proximal end 26 of housing 22 in opposition to spring 50. Injector 20 has elements to retain piston 44 in the armed position retaining potential energy in spring 50. Injector 20 further has elements for releasing piston 44 from the armed position allowing the energy stored in spring 50 to urge a distal axial movement of piston 44. The movement of piston 44 engages stopper 36 and causes stopper 36 to move axially through chamber 32 to eject liquid 33 through orifice 42. Stream S of liquid 33 formed at orifice 42 will make a hypodermic penetration when orifice 42 is placed adjacent dermal tissue. Injector 20 further has elements to substantially prevent piston 44 from being retained in the armed position once the release elements have been released.

Figure 5:
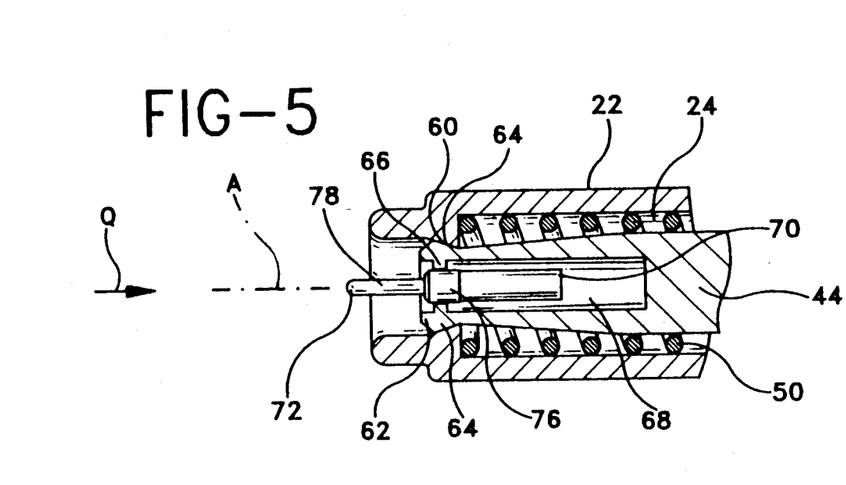
FIG. 5 is an enlarged partial cross-sectional view of the proximal portion of the injector illustrating the relationship of the several components with the housing while the piston is in the armed position.
Figure 6:
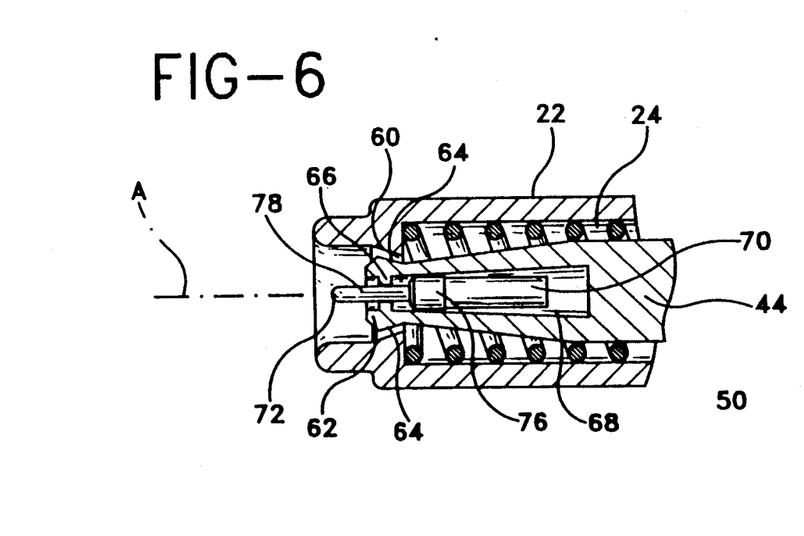
FIG. 6 is an enlarged partial cross-sectional view of the proximal portion of the injector illustrating the relationship of the several components with the housing after the release means is released.
Figure 7:
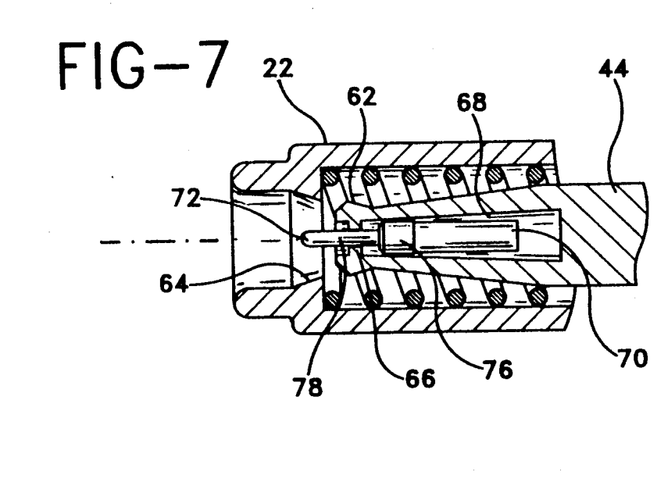
FIG. 7 is an enlarged partial cross-sectional view of the proximal portion of the injector illustrating the relationship of the several components with the housing as the piston moves distally axially.
Figure 8:
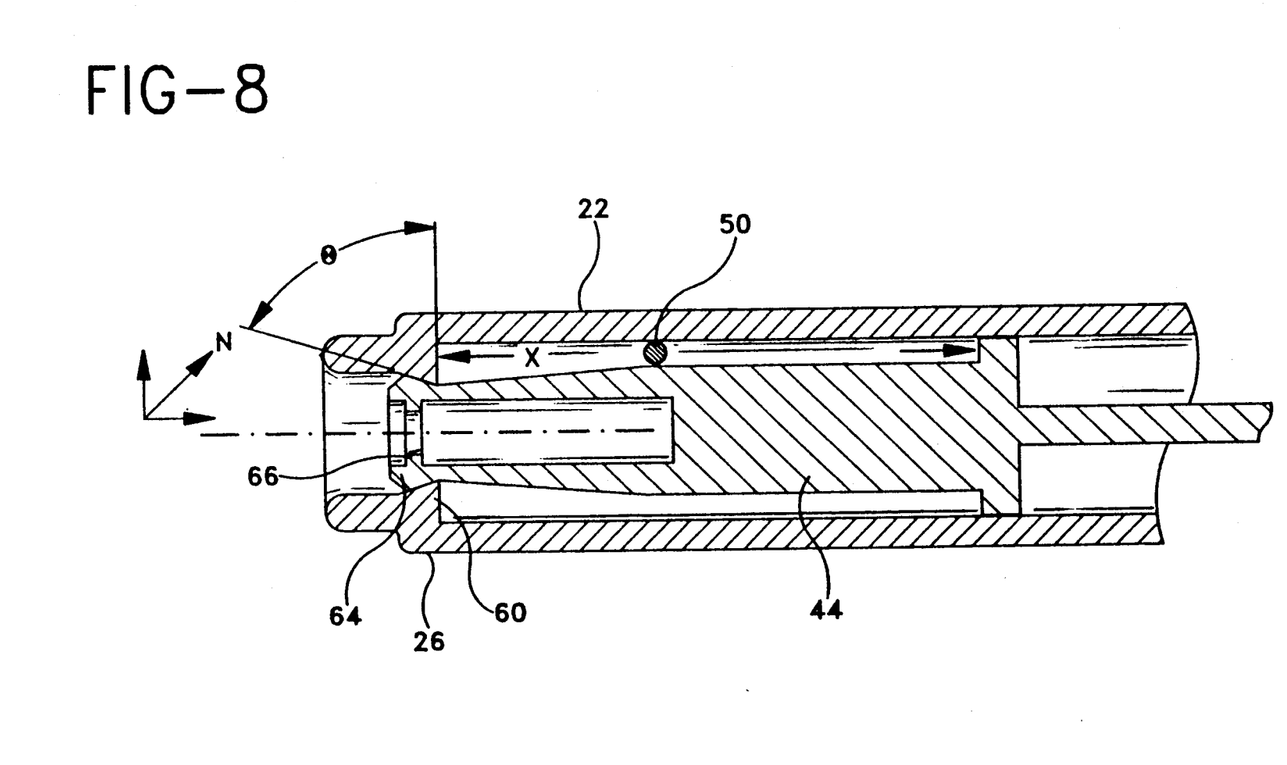
FIG. 8 is a schematic cross section of the piston and the proximal portion of the housing of a preferred embodiment of the invention.
Figure 9:
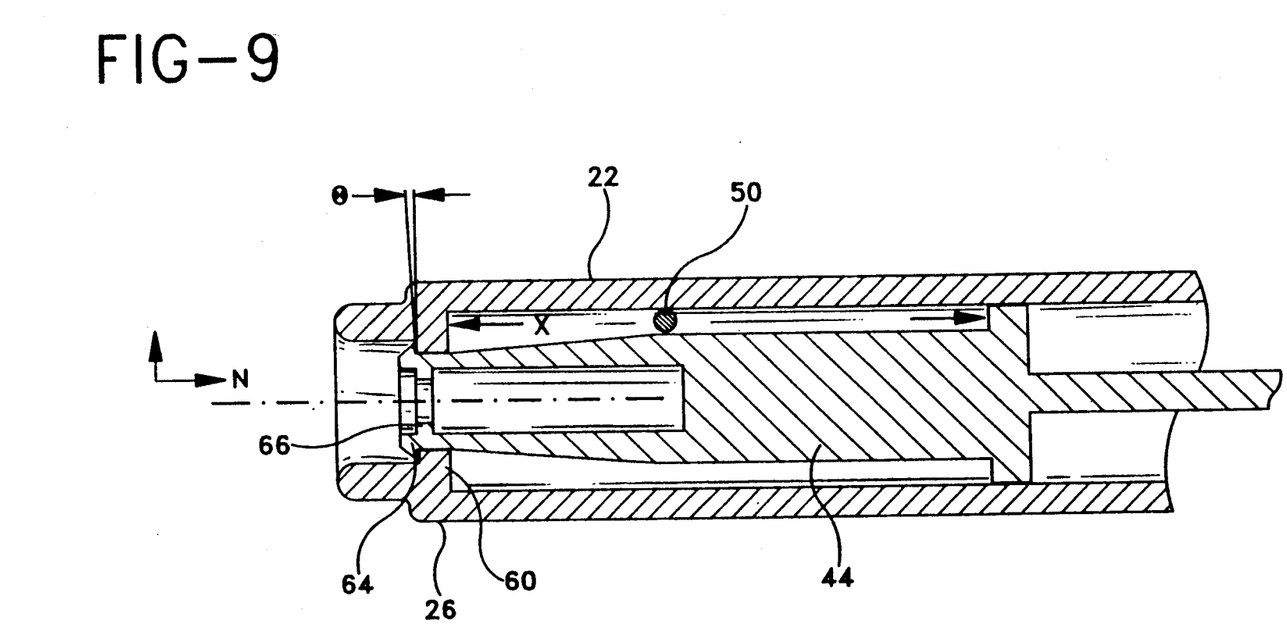
FIG. 9 is a schematic cross section of the piston and the proximal portion of the housing of the injector.

Adverting to FIGS. 5-7, an enlarged detail is shown of a preferred embodiment of the elements of injector 20 which retain piston 44 in the armed position, release piston 44 from the armed position and substantially prevent piston 44 from being retained in the armed position once injector 20 has been used.

In FIG. 5, the elements of injector 20 for retaining piston 44 in the armed position are shown. Housing 22 has an inwardly directed shoulder 60 which defines an inner dimension C transverse axis A, preferably located proximally within bore 24. In a preferred embodiment as shown, shoulder 60 is formed as a part of housing 22. As an alternate, shoulder 60 may be a separate component fixedly mounted in or engaging housing 22. Piston 44 has at least two cantilevers 62 extending proximally, each cantilever 62 includes a radially outwardly directed projection 64 for engaging shoulder 60 and a radially inwardly directed protuberance 66. Cantilevers 62 define a recess 68 in piston 44 with an interior dimension D transverse to longitudinal axis A.

Injector 20 further includes an elongate plunger 70 having a proximal end 72 and a distal end 74, positioned for slidable movement within recess 68 between cantilevers 62. Plunger 70 has a portion 76 having a larger dimension E transverse axis A relative to and distally adjacent a portion 78 having a smaller dimension F transverse axis A. When piston 44 is positioned proximally in the armed position, plunger 70 is positioned so that larger transverse dimension portion 76 is contacting protuberances 66, thereby preventing inward flexion of cantilevers 62 so that projections 64 engage shoulder 60 and retain piston 44 in the armed position.

One skilled in the art will recognize that cantilevers 62 may be integrally formed as part of piston 44 and resilient as in the preferred embodiment shown herein, or in the alternate, be separate elements attached to the piston.

Piston 44 is released from the armed position by application of an external distal axial force Q which causes axial movement of plunger 70 relative to protuberances 66. Plunger larger portion 76 is moved distally axially placing small dimension portion 78 adjacent protuberances 66. The placement of small dimension portion 78 adjacent protuberances 66 allows inward flexion of cantilevers 62 thereby allowing disengagement of projections 64 from shoulder 60. The disengagement of projections 64 from shoulder 60 thereby allows preferred spring 50 to urge distal axial movement of piston 44.

The distal axial movement of piston 44 results in piston 44 engaging stopper 36, moving the stopper through chamber 32 to eject contained liquid 33 in stream S through orifice 42 so that the stream will make a hypodermic penetration when orifice 42 is positioned adjacent dermal tissue.

As is shown in FIGS. 6 and 7, distal axial movement of piston 44 draws plunger 70 into housing 22. When small dimension portion 78 is adjacent inward protuberances 66, cantilever protuberances 66 contain plunger 70 at large dimension portion 76 adjacent small dimension portion 78 in recess 68, thereby causing withdrawal of plunger 70 into bore 24 of housing 22 with distal movement of piston 44.

Portion 78 of plunger 70 may proximally extend beyond housing 22 when piston 44 is retained in the proximal armed position to receive axial force Q for moving plunger 70 distally axially. Alternatively, as seen in FIG. 4, an external button 73 may be placed on housing 22 to detachably cooperate with and contact plunger proximal portion 72 for transmission of axial force Q to plunger 70.

As described above and shown schematically in FIGS. 8 and 9, piston 44 is positioned proximally in housing 22 and retained in the armed position by the engagement of shoulder 60 by projections 64 on cantilevers 62. An axial tensile force is imparted on piston 44 to compress spring 50 between annular flange 45 on piston 44 and proximal portion 26 of housing 22. Generally, in prior art spring powered devices, when a piston is retained in the armed position, a constant axial tensile force is applied to the housing elements. This constant load requires that the housing elements be constructed from materials which do not deform under the resultant stress. Generally metals are used, adding both to the difficulty of manufacture and mass of the device. In the present invention, the normal force N necessary to hold spring 50 in the compressed position is applied to shoulder 60 at proximal portion 26 of housing 22 when the piston is positioned proximally and plunger large diameter portion 76 is adjacent inward protuberance 66. Force N has an axial component and a radial component. In cases where the interface between shoulder 60 and projections 64 is nearly transverse axis A, i.e. angle theta approaches zero, the radial component of N is small with respect to the axial component. As in the case of the preferred embodiment where angle theta is about 70°, the radial component is large with respect to the axial component. In all cases, when the piston 44 is retained in the proximal position, the housing 22 central portion 23 is not subject to an axial load except when the release means is released.

Adverting to FIG. 5, the presence of plunger large portion 76 adjacent cantilever inward protuberance 66 prevents inward flexion of cantilevers 62, thereby forcing projections 64 against shoulder 60. This conversion of an axial force to primarily a radial force on housing 22 has the result that housing central portion 23 is not subject to a significant axial force when piston 44 is retained in the armed position. Housing central portion 23 therefore does not have a materials requirement that it not deform under axial load, which the prior art spring powered devices have had to contend with. The instant invention housing 22, piston 44 and plunger 70 may be formed from thermoplastics such as acrylonitrile/butadiene/styrene, polypropylene, polyethylene, polycarbonate, polyacetal, polyesters and the like. Further, as shown in FIG. 4, since the retention load is concentrated in the shoulder area of the housing, shoulder 60 may be integrally formed as part of housing 22 or another material such as a metal insert may be bonded, adhesively, mechanically and the like, to housing 22 as a separate component.

Referring again to FIG. 4, reservoir 30 is mounted at distal end 28 of housing 22 by interacting element 80 on end 28 and a conjugate element 82 on open end 34 of the reservoir. These elements may be threads or snap-fit elements and in a preferred embodiment, elements 80 and 82 would be constructed to be substantially non-releasable once engaged.

Distal second end 40 of the reservoir 30 has an orifice 42 to form a stream of liquid 33 when resilient stopper 36 is moved distally in chamber 32. Orifice 42 preferably is integrally formed in a single step with formation of reservoir 30. Reservoir 30 may be formed from a thermoplastic such as polypropylene, acrylonitrile/butadiene/styrene, polyethylene, polyacetal, polyester and the like. Orifice 42 preferably is sealed by a cap 84 which would be removed prior to use of the injector. Device 20 preferably has tamper evidence elements to provide visual evidence that cap 84 has been moved from its initial position. The tamper evidence elements may include a frangible seal connecting cap 84 to reservoir 30.

Plunger 78 preferably has elements for preventing its unintentional movement and release of piston 44 such as a cap 86 or cover over proximal end 26 of the housing and tamper evidence elements to provide visual evidence that the cap or cover has been moved from its initial position. The tamper evidence elements may include a frangible seal.

Reference has been made to the presently invented needleless injection device being single use. The elements in a preferred embodiment of the device which serve to render the present invention single use or substantially non-reusable and which also would generally render the device resistant to reuse include but are not limited to the non-releaseability of the reservoir attachment elements to the housing and the withdrawal of the elongate plunger into the housing by the piston when it is released. In order to overcome these provisions for rendering the device single use or to reuse it, the housing of the device must be breached, rendering it substantially non-functional.

Thus, it can be seen that the present invention provides a simple to manufacture, easily used, difficult to misuse needleless injector which will be suitable for stand-by self administration of injectable medicaments.

What is claimed is:

1. An operable single use needleless hypodermic injector comprising:

an elongate housing having a proximal end, a distal end, a hollow bore therethrough and a longitudinal axis;

a reservoir at said distal end of said housing, said reservoir having a generally cylindrical chamber defining a longitudinal axis for containing an injectable liquid, said chamber being axially aligned with said longitudinal axis of said housing, said reservoir having a first open end adjacent said housing, a resilient stopper mounted slidably within said chamber, said stopper for sealing said chamber and for ejecting the liquid from said chamber, and a distal second end of said reservoir having an orifice in fluid communication with said chamber, said orifice serving to form a stream of the liquid when said stopper is moved distally in said chamber; and an elongate piston mounted for axial movement within said bore having a proximal end and a distal end, said injector having biasing means for axially biasing said piston to said distal end of said housing, said piston having an armed position wherein said piston is positioned proximally in said housing in opposition to said biasing means, said biasing means thereby having potential energy, retention means for retaining said piston in said armed position, release means for releasing said piston from said armed position and allowing said energy of said biasing means to urge a distal axial movement of said piston, said movement of said piston to engage and to cause a distal axial movement of said stopper through said chamber thereby ejecting the liquid through said orifice, so that the stream of the liquid being formed at said orifice will make a hypodermic penetration when said orifice is placed adjacent dermal tissue, and means for preventing said piston from being retained in said armed position after said release means is released.

2. The injector of claim 1 wherein said biasing means for distally axially biasing said piston is a spring.

3. The injector of claim 2 wherein said spring is a helical compression spring coaxially mounted about said piston, said spring being compressed between said housing and said piston when said piston is in said armed position.

4. The injector of claim 3 wherein said retention means is configured so that the axial force necessary to compress said spring between said piston and said housing is applied to said housing primarily as a radial force, said housing thereby not being subject to said axial force when said piston is retained in said armed position.

5. The injector of claim 1 further including:

an annular inwardly directed shoulder defining an inner dimension transverse to said longitudinal axis located within said housing;

said elongate piston having at least two cantilevers extending proximally therefrom, each of said cantilevers including a radially outwardly directed projection for engaging said shoulder and a radially inwardly directed protuberance, said cantilevers defining a recess having an inside dimension transverse said longitudinal axis;

an elongate plunger having a proximal end and a distal end being positioned for slidable movement within said recess, said plunger having a large dimension portion transverse said longitudinal axis and a small dimension portion transverse said longitudinal axis located proximally from and adjacent said large dimension portion;

said plunger being positioned so that said large dimension portion is contacting said protuberances when said piston is in said armed position, thereby preventing inward flexion of said cantilevers causing said projections on said cantilevers to engage said shoulder and to retain said piston in said armed position;

said piston being releaseable from said armed position by application of a distal axial force causing axial movement of said plunger relative to said protuberances so that said small transverse portion is adjacent said protuberances, thereby allowing inward flexion of said cantilevers so that said projections disengage said shoulder thereby releasing said piston to move distally; and said protuberances on said cantilevers being adjacent said small transverse portion of said plunger with said release means being released, thereby containing said plunger in said recess at said large dimension portion and moving said plunger distally with said distal movement of said piston.

6. The injector of claim 5 wherein said proximal end of said plunger is withdrawn to a position substantially within said housing with said distal movement of said piston so that said piston is substantially prevented from being retained in said armed position.

7. The injector of claim 5 wherein said annular inwardly directed shoulder is formed as a separate component and bonded to said housing.

8. The injector of claim 5 wherein said cantilevers are resilient.

9. The injector of claim 5 wherein said proximal end of said plunger projects from said housing when said piston is in said armed position.

10. The injector of claim 9 wherein said proximal end of said plunger projects from said housing serving as a trigger for receiving said external distal axial force for releasing said release means for releasing said piston from said armed position.

11. The injector of claim 10 having means for preventing unintentional release.

12. The injector of claim 11 having tamper evidence means for providing visual indication that said means for preventing unintentional release has been moved from its original position.

13. The injector of claim 12 wherein said tamper evidence means includes a frangible seal.

14. The injector of claim 5 wherein said proximal end of said plunger is contained within said housing and said external distal axial force for movement of said plunger is provided to said proximal end of said plunger through a button contacting said proximal end of said plunger.

15. The injector of claim 14 wherein said button has means for preventing unintentional release.

16. The injector of claim 15 having tamper evidence means for providing visual indication that said means for preventing unintentional release has been moved from its initial position.

17. The injector of claim 1 wherein said reservoir is fastened at said distal end of said housing by means of interacting elements including a first element at said distal end of said bore of said housing and a second conjugate element on said open end of said reservoir.

18. The injector of claim 17 wherein said interacting elements are threads.

19. The injector of claim 17 wherein said first and second elements are non-releasable.

20. The injector of claim 1 wherein said housing and said piston are formed from a thermoplastic.

21. The injector of claim 5 wherein said plunger is formed from a thermoplastic.

22. The injector of claim 1 wherein said distal second end with said orifice of said reservoir is sealed by a removable cap.

23. The injector of claim 22 having tamper evidence means for providing visual indication that said cap has been moved from its initial position.

24. The injector of claim 23 wherein said tamper evidence means includes a frangible seal connecting said cap and said reservoir.

25. The injector of claim 24 wherein said tamper evidence means includes a frangible seal.

26. The injector of claim 1 wherein said reservoir is formed from a thermoplastic.

27. The injector of claim 26 wherein said reservoir has means for non-releasably attaching said proximal first end of said reservoir to said distal second end of said housing and said orifice in said distal second end of said reservoir is integrally formed in a single step with said formation of said reservoir.

* * * * *